United States Patent
Suzuki et al.

(10) Patent No.: US 9,435,769 B2
(45) Date of Patent: Sep. 6, 2016

(54) ULTRASONIC TESTING SENSOR AND ULTRASONIC TESTING METHOD

(71) Applicant: MITSUBISHI HITACHI POWER SYSTEMS, LTD., Kanagawa (JP)

(72) Inventors: Yutaka Suzuki, Tokyo (JP); Hiroaki Chiba, Yokohama (JP); Takeshi Kudo, Yokohama (JP)

(73) Assignee: MITSUBISHI HITACHI POWER SYSTEMS, LTD., Kanagawa (JP)

( * ) Notice: Subject to any disclaimer, the term of this patent is extended or adjusted under 35 U.S.C. 154(b) by 36 days.

(21) Appl. No.: 14/531,233

(22) Filed: Nov. 3, 2014

(65) Prior Publication Data

US 2015/0122029 A1    May 7, 2015

(30) Foreign Application Priority Data

Nov. 7, 2013   (JP) .................................. 2013-231258

(51) Int. Cl.

| G01N 24/00 | (2006.01) |
|---|---|
| G01N 29/265 | (2006.01) |
| G01N 29/04 | (2006.01) |
| G01N 29/22 | (2006.01) |
| G01N 29/26 | (2006.01) |

(52) U.S. Cl.
CPC .......... *G01N 29/265* (2013.01); *G01N 29/043* (2013.01); *G01N 29/221* (2013.01); *G01N 29/262* (2013.01); *G01N 2291/044* (2013.01); *G01N 2291/102* (2013.01); *G01N 2291/106* (2013.01)

(58) Field of Classification Search
CPC .......................... G01N 29/221; G01N 29/262
See application file for complete search history.

(56) References Cited

U.S. PATENT DOCUMENTS

| 4,592,237 | A | | 6/1986 | Ogura et al. | |
|---|---|---|---|---|---|
| 4,890,268 | A | * | 12/1989 | Smith | .................. B06B 1/0629 310/334 |
| 5,520,184 | A | | 5/1996 | Ri | |
| 6,135,971 | A | * | 10/2000 | Hutchinson | .............. A61N 7/02 601/3 |
| 6,682,483 | B1 | * | 1/2004 | Abend | ............... G01S 7/52026 128/916 |
| 6,682,488 | B2 | * | 1/2004 | Abend | ..................... A61B 8/06 600/453 |
| 6,783,497 | B2 | * | 8/2004 | Grenon | .................... A61B 8/12 310/320 |
| 6,929,608 | B1 | * | 8/2005 | Hutchinson | .............. A61N 7/02 600/437 |
| 7,207,942 | B2 | * | 4/2007 | Ustuner | ............... A61B 8/5269 600/443 |
| 7,238,158 | B2 | * | 7/2007 | Abend | ............... G01S 7/52026 600/454 |
| 7,399,279 | B2 | * | 7/2008 | Abend | ..................... A61B 8/06 600/450 |
| 7,534,209 | B2 | * | 5/2009 | Abend | ............... G01S 7/52026 600/454 |

(Continued)

FOREIGN PATENT DOCUMENTS

| EP | 1411368 A1 | 4/2004 |
|---|---|---|
| JP | 2009-293980 A | 12/2009 |
| JP | 2013-042971 A | 3/2013 |

OTHER PUBLICATIONS http://www.mlit.go.jp/chosahokoku/h16giken/h15/pdf/0502.pdf.

(Continued)

*Primary Examiner* — Harshad R Patel
*Assistant Examiner* — Samir M Shah
(74) *Attorney, Agent, or Firm* — Mattingly & Malur, PC

(57) ABSTRACT

The transmission sensor 1T and the reception sensor 1R are disposed so as to sandwich a testing target 301 therebetween. The reception sensor 1R receives a false signal arising from a GL generated upon ML scanning by a scanning angle equal to or greater than a minimum scanning angle Φmin but equal to or smaller than a maximum scanning angle Φmax.

2 Claims, 12 Drawing Sheets

(56) References Cited

U.S. PATENT DOCUMENTS

| | | | | |
|---|---|---|---|---|
| 7,830,069 B2* | 11/2010 | Lukacs | ............... | B06B 1/0622 |
| | | | | 310/334 |
| 7,901,358 B2* | 3/2011 | Mehi | ............... | G01S 7/52017 |
| | | | | 600/447 |
| 8,316,518 B2* | 11/2012 | Lukacs | ............... | B06B 1/0622 |
| | | | | 219/121.67 |
| 9,173,047 B2* | 10/2015 | Lukacs | ............... | B06B 1/0622 |
| 9,184,369 B2* | 11/2015 | Chaggares | ......... | H01L 41/0475 |
| 9,199,100 B2* | 12/2015 | Auboiroux | ............ | A61N 7/02 |
| 2002/0049381 A1* | 4/2002 | Eck | ............... | A61B 8/00 |
| | | | | 600/447 |
| 2002/0130591 A1* | 9/2002 | Fraser | ............... | B06B 1/0622 |
| | | | | 310/334 |
| 2009/0048789 A1* | 2/2009 | Yu | ............... | G01N 29/069 |
| | | | | 702/39 |
| 2010/0251821 A1* | 10/2010 | Mizota | ............... | G01N 29/262 |
| | | | | 73/602 |
| 2011/0044133 A1 | 2/2011 | Tokita | | |
| 2012/0065504 A1* | 3/2012 | Sandrin | ............... | A61B 8/08 |
| | | | | 600/438 |

OTHER PUBLICATIONS

Extended European Search Report received in corresponding European Application No. 14003720.1 dated Apr. 10, 2015.

* cited by examiner

NOISE (GRATING LOBE) GENERATION MECHANISM

ULTRASONIC TESTING SENSOR AND ULTRASONIC TESTING METHOD

BACKGROUND OF THE INVENTION

1. Field of the Invention

The present invention relates an ultrasonic testing sensor and an ultrasonic testing method in which a sensor for transmission and a sensor for reception are used.

2. Description of the Related Art

First, a principle of a general phased array ultrasonic testing method (in the following description, ultrasonic testing is referred to as UT) is described. As illustrated in FIG. 8, ultrasonic elements (hereinafter referred to simply as elements) of a rectangular parallelepiped which configure a UT sensor are arrayed in parallel to each other. Ultrasonic wave outgoing starting time differences (hereinafter referred to as delay time periods) between the elements are adjusted so that ultrasonic waves arrive at the same time at a focus to raise the sound pressure at the focus to carry out testing or flaw detection. By detecting the delay time periods, the focal position is changed and an ultrasonic wave is scanned.

The limiting factor of the element pitch of the array sensor having the configuration described above is such as given below. When a main lobe (hereinafter referred to simply as ML) is converged to the focus, a grating lobe (hereinafter referred to simply as GL) along which the phases of the ultrasonic waves are aligned appears as depicted in FIG. 9. The generation angle $\Delta\phi$ of the GL with respect to the ML is represented by the following expression (1) (refer to, for example, page 3, line 16 of a document http://www.mlit.go.jp/chosahokoku/h16giken/h15/pdf/0502.pdf):

$$2d \cdot \sin \Delta\phi = n \cdot \lambda \quad \text{expression (1)}$$

where
- d: element pitch [mm];
- n: integer; and
- $\lambda$: ultrasonic wavelength [mm].

Where a reflection source exists in an incident direction of the GL, a false signal which is recognized in error as a reflected wave of the ML. Therefore, The element pitch of the sensor is restricted to the range in which the GL represented by the following expression (2) is not generated:

$$n \cdot \lambda/2d = \sin \theta > 1$$

$$d < \lambda/2 (n=1) \quad \text{expression (2)}$$

Meanwhile, as a method of improving the sensitivity of a phased array UT by sensor area expansion, a sensor having an ultrasonic element pitch equal to or greater than $\lambda/2$ is known (refer to, for example, JP-2009-293980-A). Further, an ultrasonic probe configured from a combination of a plurality of array sensors between which the installation angle with respect to a testing target is different is known (refer to, for example, JP-2013-42974-A).

SUMMARY OF THE INVENTION

In such a sensor as disclosed in JP-2009-293980-A, a GL appears. If a reflection source exists in a generation direction of the GL, then a false signal is generated, and therefore, it is necessary to identify the false signal from a signal generated on the ML.

In contrast, in such a probe as disclosed in JP-2013-42974-A, a plurality of array sensors between which the installation angle with respect to a testing target is different are combined to make it possible to identify a GL.

As depicted in FIG. 10, if the array sensor on the left side of the probe of the configuration just described is used for flaw detection of a reflection source, then since a ML enters, a strong echo is detected. If the central sensor is used for flaw detection, then a weak echo by a GL is detected. If the right side sensor is used for flaw detection, then no reflection wave is detected. The differences in reflection echo behavior among the array sensors are utilized to make it possible to identify reflection by the GL.

However, if it is tried to apply such a sensor as disclosed in JP-2013-42974-A to a testing target having a flat outer shape, then there is a problem that the sensor cannot be contacted directly with the testing target.

It is an object of the present invention to provide a UT sensor and a UT method by which a GL can be identified also where the sensor is installed at a flat face portion of a testing target.

To achieve the object just described, according to the present invention, there is provided an ultrasonic testing sensor including a transmission sensor configured from ultrasonic elements of a parallelepiped arrayed one-dimensionally and configured to transmit ultrasonic waves whose center frequency has a wavelength $\lambda$, and a reception sensor configured from ultrasonic elements of a parallelepiped arrayed one-dimensionally and configured to receive reflected waves of the ultrasonic waves. The reception sensor receives a grating lobe in accordance with a main lobe, the grating lobe being reflected within a testing range scanned by the main lobe having a scanning angle equal to or greater than a minimum scanning angle $\Phi$min but equal to or smaller than a maximum scanning angle $\Phi$max.

With the ultrasonic testing sensor, also where the sensor is installed at a flat face portion of a testing target, a GL can be identified. The above and other objects, features and advantages of the present invention will become apparent from the following description.

DESCRIPTION OF THE PREFERRED EMBODIMENTS

First Embodiment

An ultrasonic testing sensor and an ultrasonic testing method according to a first embodiment of the present invention are described with reference to FIGS. 1 to 4 and expressions (1), (3) and (4).

First, an outline of a GL identification method in the first embodiment is described with reference to FIG. 1. A UT sensor 1 includes a transmission sensor 1T and a reception sensor 1R. The transmission sensor 1T and the reception sensor 1R are disposed such that a testing target 301 is positioned therebetween. The transmission sensor 1T is configured from a one-dimensional array of elements (piezoelectric elements) of a parallelepiped and transmits ultrasonic waves. Also the reception sensor 1R is configured from a one-dimensional array of elements of a parallelepiped and receives a reflection wave of an ultrasonic wave generated by the testing target 301.

In the UT of the present embodiment,
(i) the position of the sensor on the testing target is measured by ultrasonic testing.

Figure 1:
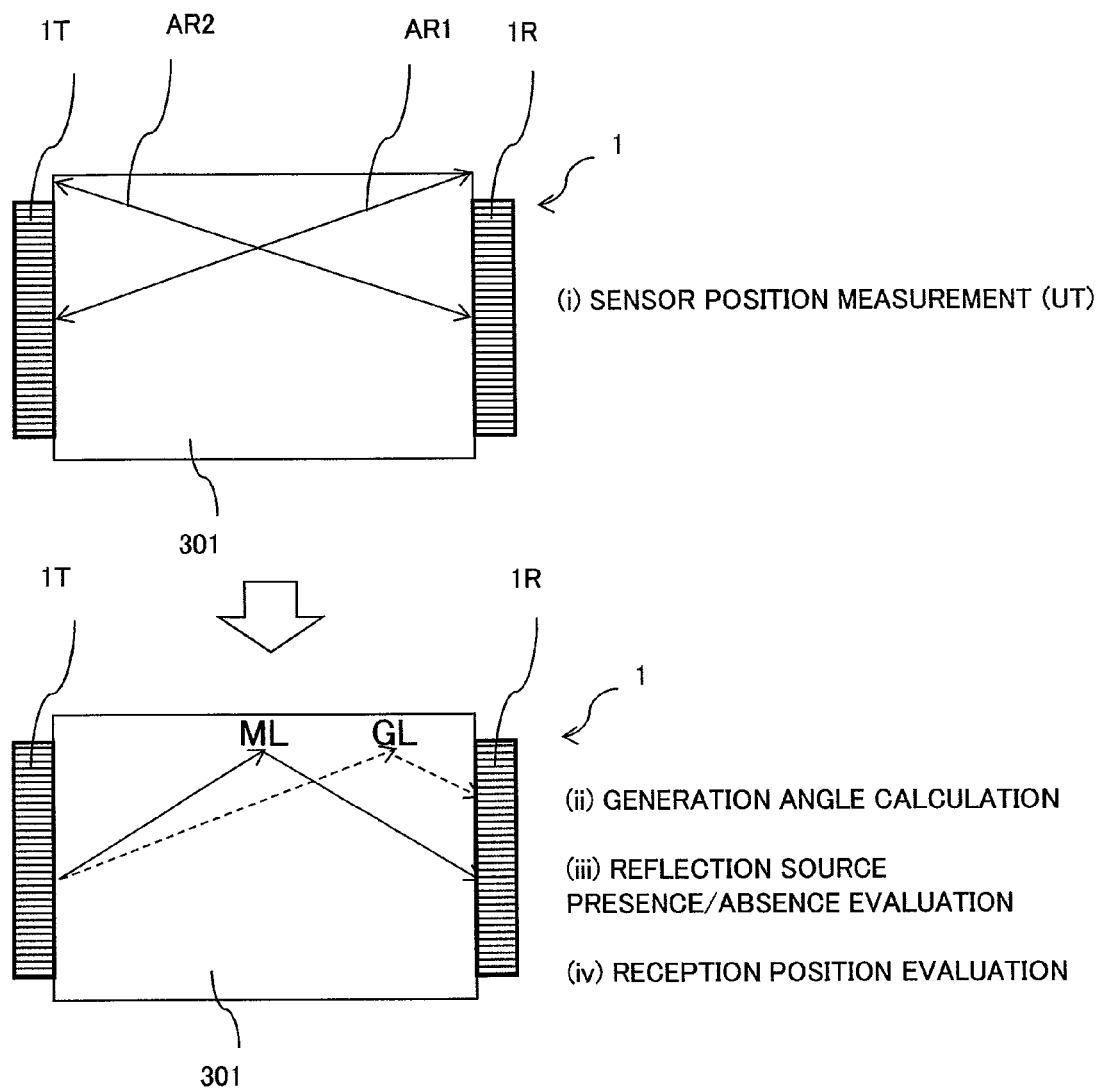
FIG. 1 is a conceptual view of a GL identification method according to a first embodiment of the present invention.

An arrow mark AR1 depicted in FIG. 1 indicates a reflected wave when an incident wave transmitted from the transmission sensor 1T is reflected by a corner of the testing target 301. Meanwhile, another arrow mark AR2 indicates a reflected wave when an incident wave transmitted from the reception sensor 1R is reflected by another corner of the testing target 301. The distance and the angle between the transmission sensor 1T or the reception sensor 1R and a characteristic echo source having a high ultrasonic wave reflection factor such as a corner of the testing target 301 are measured to measure the position of the transmission sensor 1T and the reception sensor 1R with respect to the testing target 301. Further, the accuracy in position measurement may be improved by transferring ultrasonic waves between the transmission sensor 1T and the reception sensor 1R and measuring the relative positions of the sensors.
(ii) The expression (1) is solved from the pixel pitch to calculate a GL generation angle,
(iii) it is evaluated (determined) whether there exists a reflection source in the GL incident direction, and
(iv) when there is a reflection source in the GL incident direction, the reception position of the reflected wave is measured (evaluated). Since the reception position of the ML and the reception position of the GL on the reception sensor 1R are different from each other, the ML and the GL are identified from each other on the basis of a result of the measurement of the reception position.

Figure 2A:
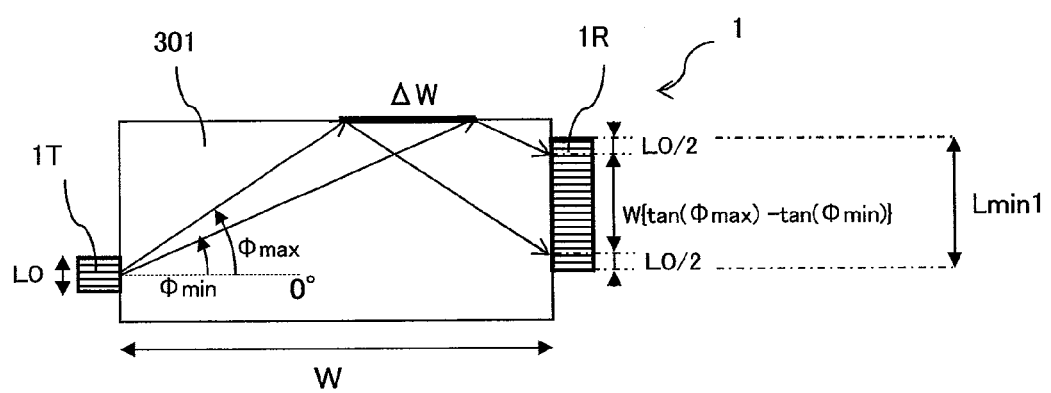
FIG. 2A is a diagrammatic view illustrating a minimum length of a reception sensor necessary in ultrasonic testing in which identification of a GL is not involved.
Figure 2B:
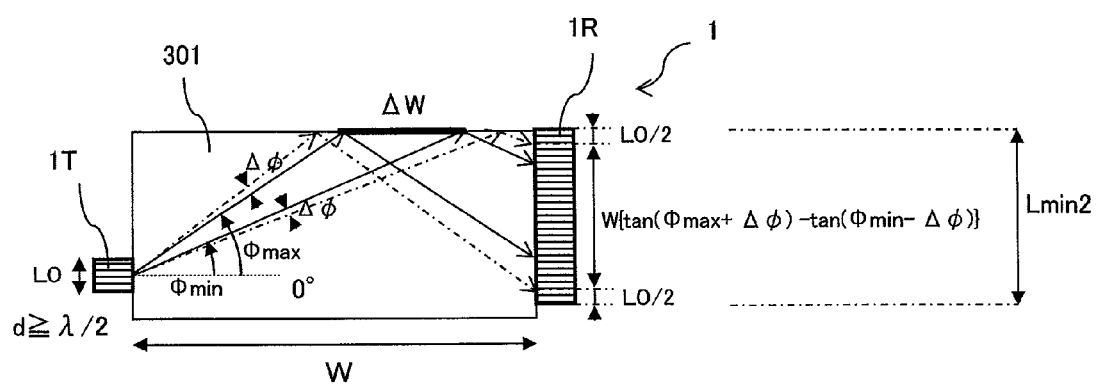
FIG. 2B is a diagrammatic view of an ultrasonic testing sensor according to the first embodiment of the present invention.

FIGS. 2A and 2B depict a sensor configuration necessary for carrying out the UT method according to the first embodiment of the present invention. FIG. 2A is a view illustrating a minimum length Lmin1 of the reception sensor necessary in the UT which does not involve identification of a GL. The minimum length Lmin1 is represented by the following expression (3):

$$Lmin1 = W\{\tan(\Phi max) - \tan(\Phi min)\} + L0 \quad \text{expression (3)}$$

where
  W: testing target width (specimen width);
  Φmax: maximum value of the ultrasonic wave scanning angle;
  Φmin: minimum value of the ultrasonic wave scanning angle; and
  L0: length of the sensor necessary for flaw detection.

Referring to FIG. 2A, a testing range ΔW indicated by a thick line is scanned over a scanning angle equal to or greater than Φmin but equal to or smaller than Φmax. The length L0 of the transmission sensor 1T necessary for flaw detection is a minimum value of the length of the transmission sensor 1T necessary for detection of a flaw of a predetermined size and is a predetermined value.

FIG. 2B is a schematic view depicting a configuration of the UT sensor 1 according to the first embodiment of the present invention. As depicted in FIG. 2B, in the present embodiment, since the reception angle becomes greater by the generation angle Δϕ of the GL, the minimum length Lmin2 of the reception sensor 1R necessary for ultrasonic testing is represented by the following expression (4):

$$Lmin2 = W\{\tan(\Phi max + \Delta\phi) - \tan(\Phi min - \Delta\phi)\} + L0 \quad \text{expression (4)}$$

In this manner, in the present embodiment, in order to identify the ML and the GL from each other on the basis of the reception position of a reflected wave, the reception sensor 1R which is longer than a sensor of the conventional UT method which does not involve identification of the ML and the GL is used. Consequently, it is made possible by the reception sensor 1R to receive the GL which appears upon ML scanning and is reflected by the testing range ΔW.

Figure 3:
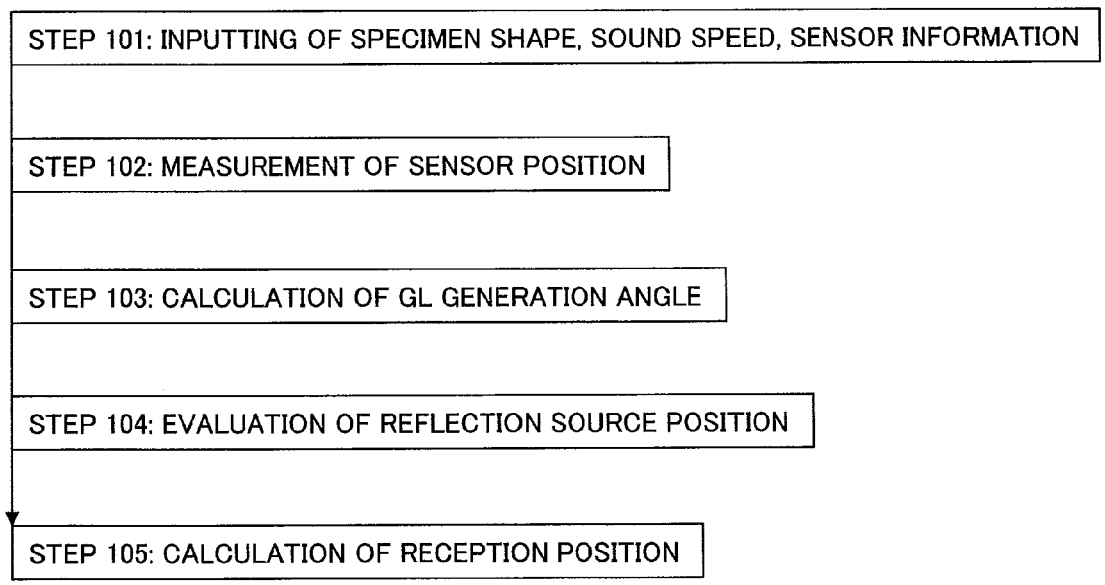
FIG. 3 is a flow diagram of an ultrasonic testing method according to the first embodiment of the present invention.
Figure 4:
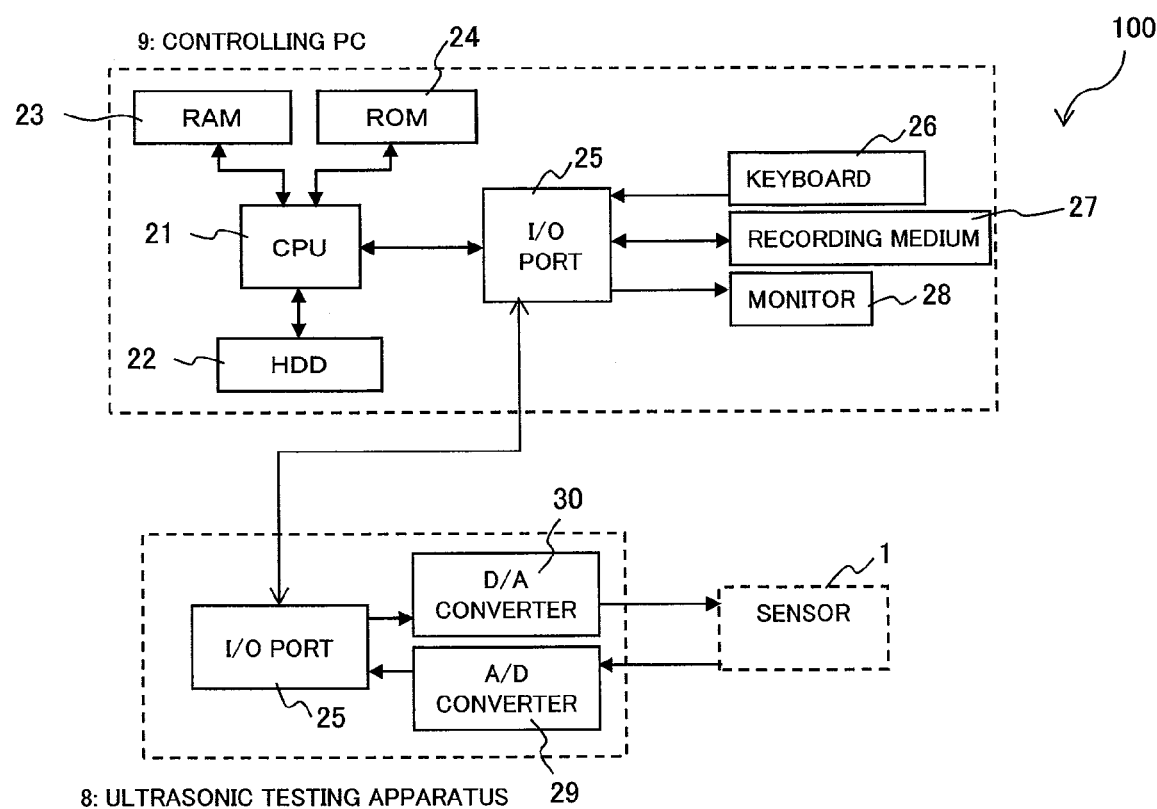
FIG. 4 is a flow diagram of an ultrasonic testing system including the ultrasonic testing sensor according to the first embodiment of the present invention.

Now, a GL identification step in the first embodiment is described with reference to FIGS. 3 and 4. FIG. 3 is a flow diagram of the UT method according to the first embodiment. FIG. 4 is a flow diagram of a UT system 100 which includes the UT sensor 1 according to the first embodiment of the present invention. The UT system 100 is configured from a controlling PC 9, a UT apparatus 8 and the UT sensor 1. The UT apparatus 8 includes an I/O port 25, and an A/D converter 29 and a D/A converter 30 which are connected to the UT sensor 1.

A step 101 depicted in FIG. 3 is an inputting step of a specimen shape, a specimen sound speed, an ultrasonic testing position, a component number and an element pitch to the controlling PC 9. The input parameters mentioned are inputted using one or more of apparatus including a keyboard 26 and a recording medium 27 of the controlling PC 9 and transmitted to a CPU 21 through an I/O port 25 of the controlling PC 9. Then, the input parameters are recorded into one or more of recording media including a random access memory (RAM) 23 and a hard disk drive (HDD) 22. As the recording medium 27, a DVD, a Blu-ray (registered trademark) or the like is used. Meanwhile, as the hard disk drive 22, a magnetic recording medium drive, an SSD drive or the like is used.

A step 102 is a sensor position measurement step on the testing target 301. The distance and the angle between a reflection source position such as the angle of the testing target 301 and the transmission sensor 1T and reception sensor 1R are measured by UT, and the sensor position and the relative position between the sensors on the testing target 301 are measured.

A step 103 is a calculation step of the GL generation angle. A calculation program of the expression (1) stored in one or more of recording media including a read only memory (ROM) 24, the random access memory 23 and the hard disk drive 22 is executed by the CPU 21 to calculate the GL generation angle Δϕ. A result of the calculation is stored into one or more of the recording media including the random access memory 23 and the hard disk drive 22 and displayed on a monitor 28 through the I/O port 25.

A step 104 is an evaluation step of whether there exists a reflection source in the GL generation direction. Whether there exist a reflection source in the GL generation direction is evaluated by the CPU 21 from the testing target shape inputted at step 101 and the measurement result of the sensor position on the testing target measured at step 102. If there exists a reflection source, then the reception position is calculated. A result of the calculation is stored into one or more of the recording media including the random access memory 23 and the hard disk drive 22 and is displayed on the monitor 28 through the I/O port 25.

A step 105 is a measurement step of the reception position of a reflected wave on the reception sensor 1R. The reception position is measured from the position of the element of the reception sensor 1R at which the reception intensity is highest by the CPU 21. A result of the measurement of the reception position is stored into one or more of the storage media including the random access memory 23 and the hard disk drive 22 and is displayed on the monitor 28 through the I/O port 25.

Further, the reception position of the GL calculated at step 104 and the measured position of a reflected wave are compared with each other to evaluate whether the received signal is a false signal generated from the GL.

As described above, with the present embodiment, also where the sensor is installed at a flat face portion of a testing target, a GL can be identified. Therefore, it is possible to raise the sensitivity and the S/N ratio of the phased array UT.

Second Embodiment

Figure 5:
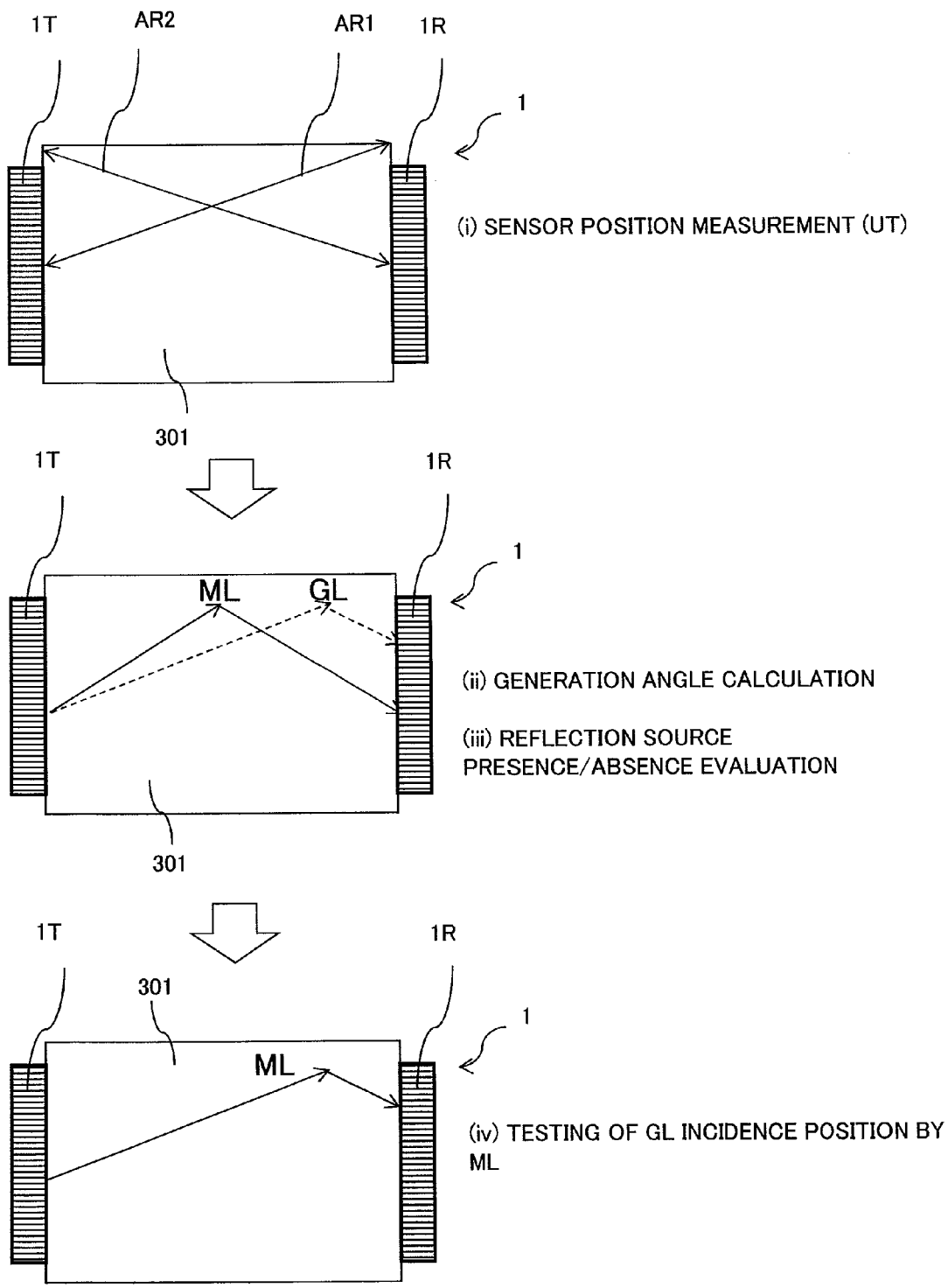
FIG. 5 is a conceptual view of a GL discrimination method according to a second embodiment of the present invention.

A UT sensor and a UT method according to a second embodiment of the present invention are described with reference to FIGS. 5 to 7 and the expressions (1) and (5). It is to be noted that, in FIGS. 5 to 7, like elements to those in FIGS. 1 to 4 are denoted by like reference characters.

First, an outline of a GL identification method according to the second embodiment is described with reference to FIG. 5.

Also in the ultrasonic testing in the present embodiment, similarly as in the first embodiment, (i) the position of the sensor on the testing target is measured by ultrasonic testing;

(ii) the expression (1) is solved from the pixel pitch to calculate a GL generation angle; and (iii) it is evaluated (determined) whether there exists a reflection source in the GL incident direction.

The ultrasonic testing in the present embodiment is different from that in the first embodiment in that (iv) when there exists a reflection source, a ML is caused to enter in the GL generation direction and the reflection intensities upon incidence of a GL and upon incidence of the ML are compared with each other to identify the GL.

Figure 6A:
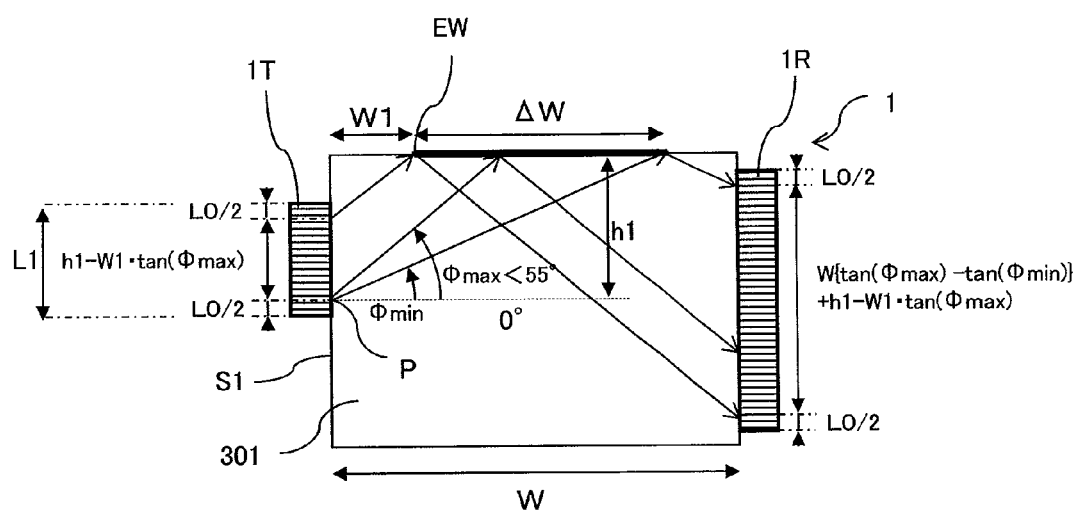
FIG. 6A is a diagrammatic view of a minimum length of a transmission sensor necessary in ultrasonic testing in which identification of a GL is not involved.
Figure 6B:
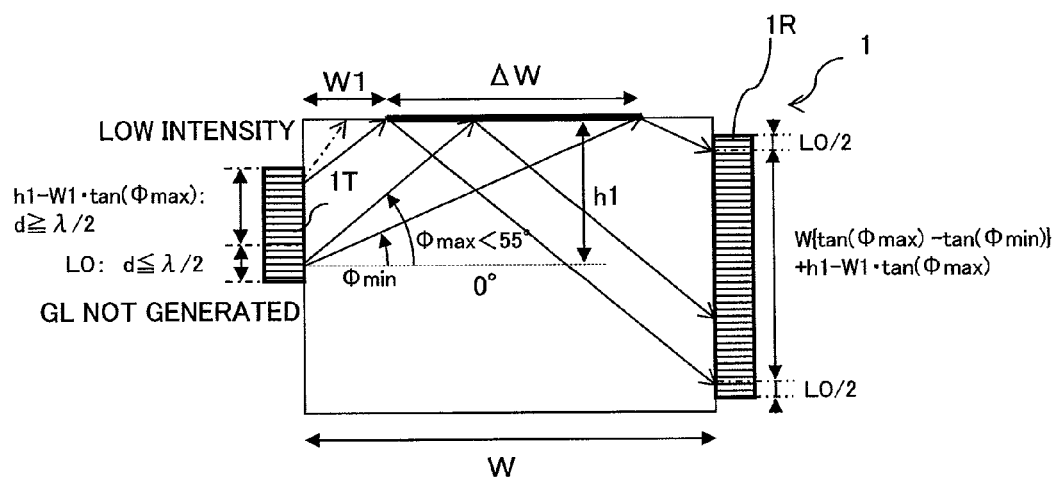
FIG. 6B is a schematic view depicting a configuration of an ultrasonic testing sensor according to the second embodiment of the present invention.
Figure 7:
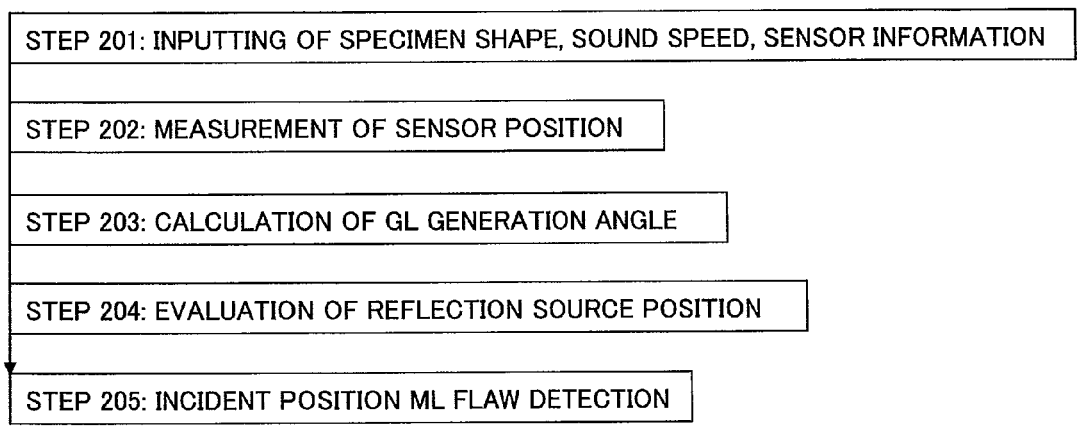
FIG. 7 is a flow diagram of an ultrasonic testing method according to the second embodiment of the present invention.
Figure 8:
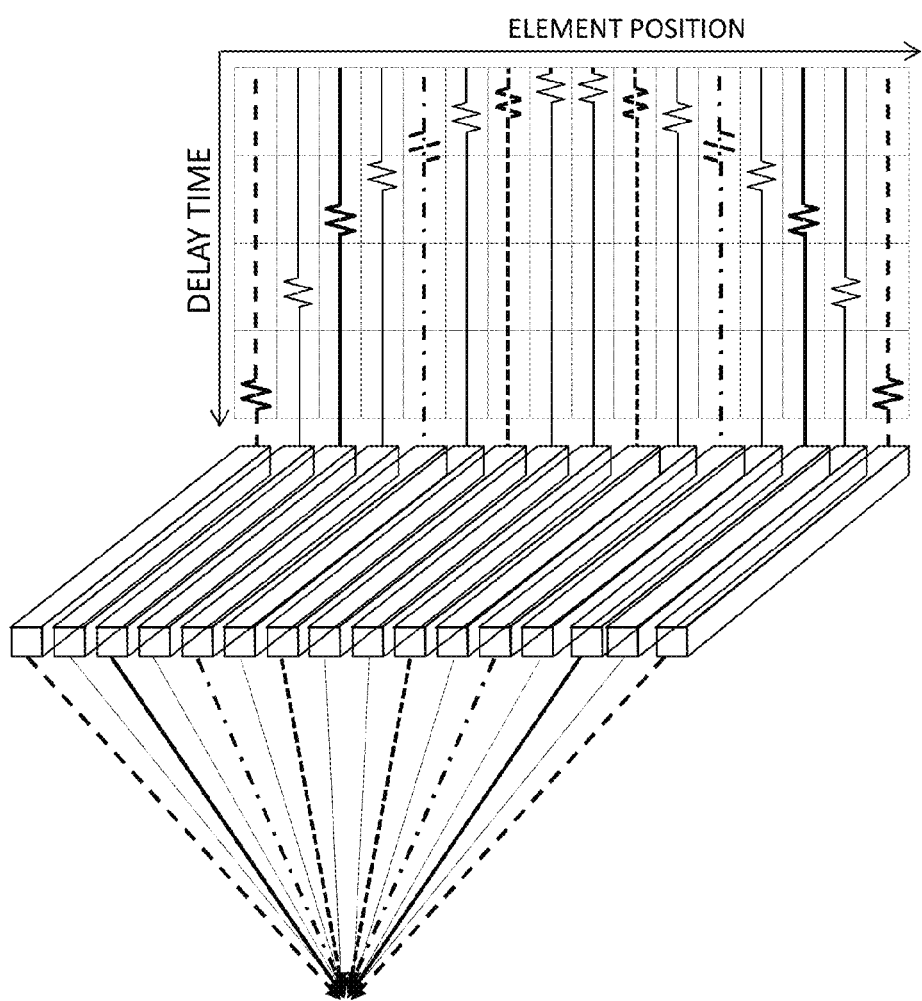
FIG. 8 is a diagrammatic view illustrating a principle of a phased array ultrasonic testing method.
Figure 9:
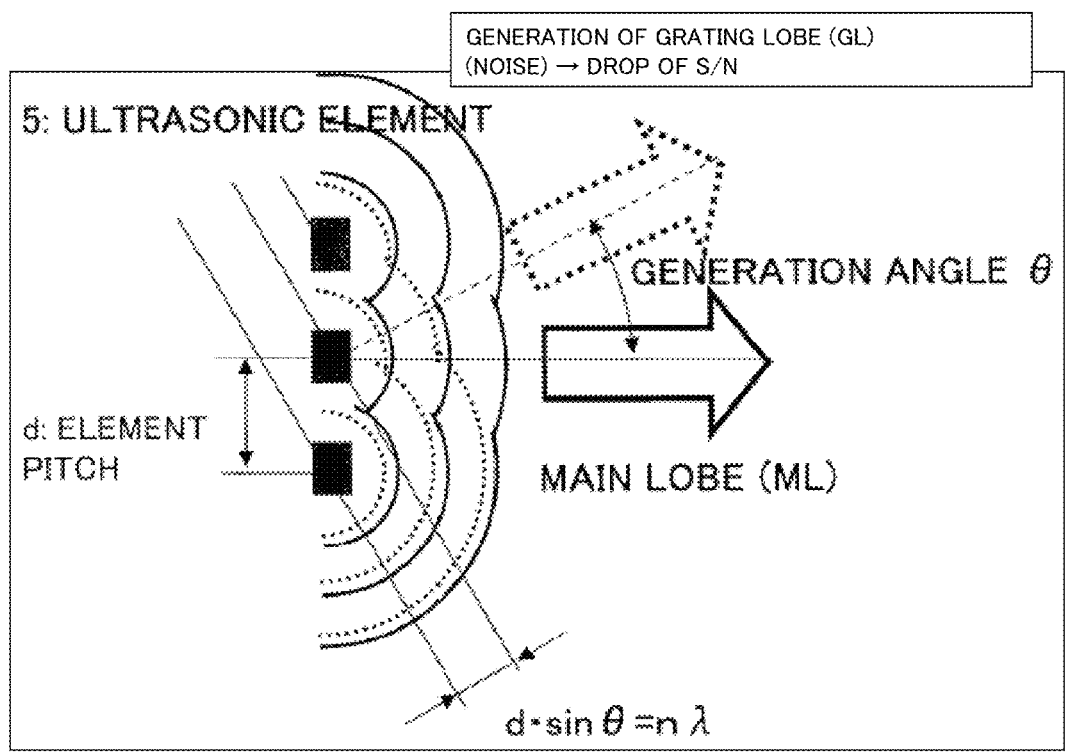
FIG. 9 is a diagrammatic view illustrating a generation mechanism of a GL.
Figure 10:
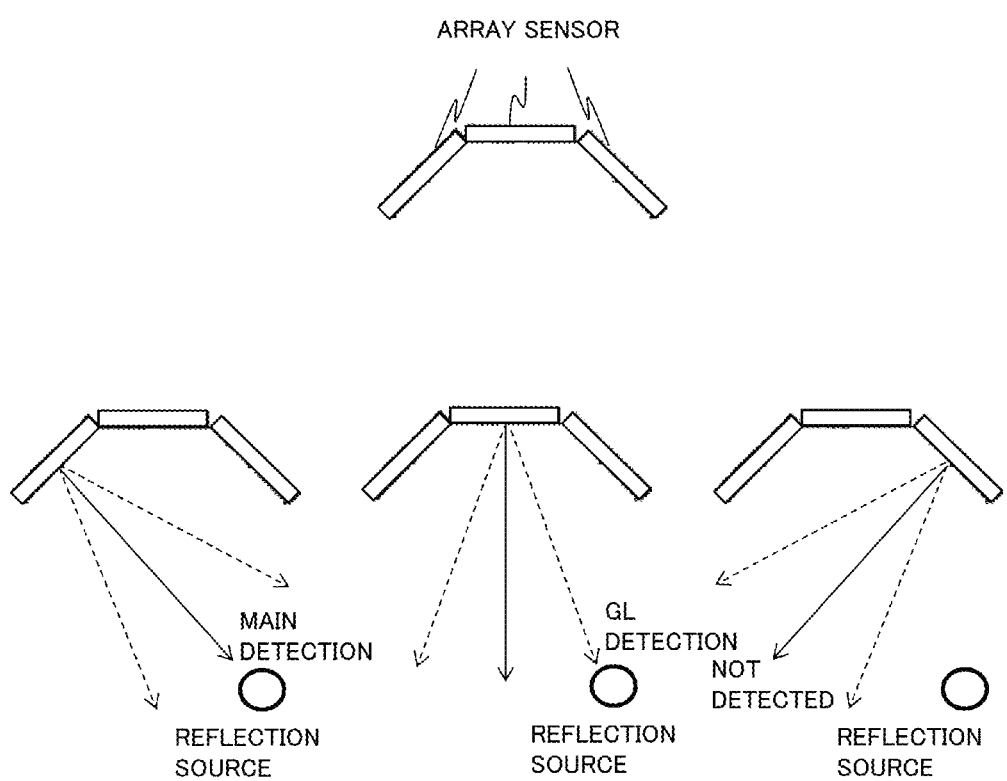
FIG. 10 is a diagrammatic view illustrating an identification method of a GL using a sensor configured from a combination of a plurality of array sensors between which the installation angle with respect to a testing target is different.

A sensor configuration in the present embodiment is detected in FIGS. 6A and 6B. FIG. 6A is a diagrammatic view illustrating a minimum length L1 of the transmission sensor necessary in a conventional UT which does not involve identification of the GL. The minimum length L1 is represented by the following expression (5):

$$L1 = h1 - W1 \cdot \tan(\Phi max) + L0 \qquad \text{expression (5)}$$

where h1: distance between the testing position and the minimum scanning angle outgoing center position; and W1: distance from the transmission sensor installation position to the testing target position.

In order for the UT sensor not to generate a GL, it is necessary to set the element pitch equal to or smaller than $\lambda/2$ over the overall extent of the minimum length L1.

On the other hand, the length Lt of the transmission sensor 1T in the present embodiment depicted in FIG. 6B is set to Lt≥L1 and the element pitch d is set equal to or smaller than $\lambda/2$ within the range of ±L0/2 from the minimum scanning angle outgoing center position. By setting the length Lt and the element pitch d in this manner, the sensor has a configuration which does not generate a GL from the ultrasonic wave outgoing position of the minimum scanning angle.

Further, the maximum scanning angle is set to a maximum value of 55 degrees at which the ultrasonic wave reflection efficiency is high and the incident angle of the GL is set to 55 degrees or more, namely, to an angle at which the reflection efficiency is low. In this case, if flaw detection is carried out at the opposite ends of the transmission sensor, then since a GL is not generated, the identification is unnecessary. Further, within the range of the length other than ±L0/2 from the minimum scanning angle outgoing center position, since the GL can be identified by the ultrasonic testing method according to the present embodiment, it is possible to set the element pitch equal to or greater than $\lambda/2$.

Therefore, it is possible to decrease the number of elements of the transmission sensor 1T. Further, different from the first embodiment, the GL can be identified even if the length of the reception sensor 1R is set to a length of the reception sensor in the conventional UT represented by the expression (3) given hereinabove.

Now, the GL identification step in the second embodiment is described with reference to FIGS. 7 and 4. FIG. 7 is a flow diagram of the UT method according to the second embodiment of the present invention.

A step 201 is an inputting step of a specimen shape, a specimen sound speed, an ultrasonic testing position, a component number and an element pitch to the controlling PC 9 similarly as at step 101.

A step 202 is a sensor position measurement step on the testing target 301 similarly as at step 102.

A step 203 is a calculation step of the GL generation angle similarly as at step 103.

A step 204 is an evaluation step of whether there exists a reflection source in the GL generation direction similarly as at step 104.

A step 205 is a step of carry out flaw detection using the ML in the GL generation direction. Since the ML is higher in intensity than the GL, when high reflection is measured upon incidence of the ML, it can be determined that this is noise generated by reflection of the GL. If strong reflection is measured when the ML is caused to enter in the calculated GL generation direction, then this is determined as a false signal.

As described above, with the present embodiment, a GL can be identified also when the sensor is installed at a flat face portion of a testing target. Therefore, it is possible to raise the sensitivity and the S/N ratio of the phased array UT.

It is to be noted that the present invention is not limited to the embodiments described hereinabove but allows various modifications. The embodiments described above are intended to facilitate understandings of the present invention, and the present invention is not necessarily limited to a configuration which includes all components described hereinabove. Also it is possible to replace part of the configuration of a certain embodiment into a configuration of another embodiment, and also it is possible to add a configuration of a certain embodiment to the configuration of another embodiment. Also it is possible to add, delete or replace part of a configuration of each embodiment to, from or with a different configuration.

Further, in the UT in the first embodiment, the step 205 may be carried out after the step 105.

Further, the reception sensor 1R in the first embodiment may be used in the UT method in the second embodiment, and the transmission sensor 1T in the second embodiment may be used in the UT method in the first embodiment.

What is claimed is:

1. An ultrasonic testing method, comprising the steps of:
calculating a generation angle $\Delta\phi$ of a grating lobe;
evaluating, on the basis of a shape of a testing target and positions of a transmission sensor and a reception sensor with respect to the testing target, whether there exists a reflection source in a grating lobe generation direction;
measuring a reception position of a reflected wave by the reception sensor; and
comparing the reception position of the grating lobe based on the calculated generation angle $\Delta\phi$ and the measured reception position of the reflected wave with each other to evaluate whether the reflected wave is a reflected wave of the grating lobe.

2. The ultrasonic testing method according to claim 1, further comprising the steps of:
transmitting a main lobe in the grating lobe generation direction; and
determining, when a reflected wave by the main lobe is measured at the reception position of the grating lobe based on the calculated generation angle $\Delta\phi$, that the reflected wave is noise by the grating lobe.

* * * * *